（12）United States Patent
Taguchi et al.

(10) Patent No.: US 9,919,164 B2
(45) Date of Patent: Mar. 20, 2018

(54) APPARATUS, METHOD, AND PROGRAM FOR PROCESSING MEDICAL IMAGE, AND RADIOTHERAPY APPARATUS

(71) Applicants: Kabushiki Kaisha Toshiba, Minato-Ku (JP); National Institute of Radiological Sciences, Chiba-Shi (JP)

(72) Inventors: Yasunori Taguchi, Kawasaki (JP); Yukinobu Sakata, Kawasaki (JP); Ryusuke Hirai, Shinagawa (JP); Kyoka Sugiura, Kawasaki (JP); Tomoyuki Takeguchi, Kawasaki (JP); Shinichiro Mori, Sakura (JP); Fumi Maruyama, Miura (JP)

(73) Assignees: KABUSHIKI KAISHA TOSHIBA, Minato-ku (JP); National Institute of Radiological Sciences, Chiba-Shi (JP)

( * ) Notice: Subject to any disclaimer, the term of this patent is extended or adjusted under 35 U.S.C. 154(b) by 150 days.

(21) Appl. No.: 14/944,672

(22) Filed: Nov. 18, 2015

(65) Prior Publication Data

US 2016/0136458 A1    May 19, 2016

(30) Foreign Application Priority Data

Nov. 19, 2014 (JP) .................................. 2014-234672

(51) Int. Cl.
*A61B 6/00* (2006.01)
*G06T 7/00* (2017.01)
(Continued)

(52) U.S. Cl.
CPC ............ *A61N 5/1049* (2013.01); *A61B 6/032* (2013.01); *A61B 6/12* (2013.01); *A61B 6/5223* (2013.01);
(Continued)

(58) Field of Classification Search
CPC ......... G06T 7/0012; G06T 7/11; G06T 7/174; G06T 7/194; G06T 2207/10116;
(Continued)

(56) References Cited

U.S. PATENT DOCUMENTS 7,545,965 B2    6/2009  Suzuki et al. ................. 382/128
2006/0182326 A1*  8/2006  Schildkraut et al. ......... 382/132
(Continued)

FOREIGN PATENT DOCUMENTS

DE    10 2009 057 066 A1    6/2011    ............... A61B 6/03
DE    10 2011 080 371 B4    1/2014    ............... A61N 5/10
(Continued)

OTHER PUBLICATIONS

Office Action dated Aug. 2, 2016 in German Patent Application No. 10 2015 014 908.3 (with English language translation).
(Continued)

*Primary Examiner* — Andrew W Johns
(74) *Attorney, Agent, or Firm* — Oblon, McClelland, Maier & Neustadt, L.L.P.

(57) ABSTRACT

According to one embodiment, a medical image processing apparatus, includes: a first acquisition unit; a second acquisition unit; and a part-removed image generation unit, wherein the first acquisition unit is adapted to acquire a first radiograph that is a virtual radiograph generated to have a specified part or a predetermined part, among parts included in volume data indicative of a three-dimensional structure of an inside of a body of a patient, being emphasized, the second acquisition unit is adapted to acquire a second radiograph of the inside of the body of the patient, and the part-removed image generation unit is adapted to generate a part-removed image by removing the specified or predeter-
(Continued)

mined part or parts other than the specified or predetermined part from the second radiograph with reference to the first radiograph.

6 Claims, 12 Drawing Sheets

(51) Int. Cl.
    *A61N 5/10*     (2006.01)
    *G06T 11/00*     (2006.01)
    *A61B 6/03*     (2006.01)
    *A61B 6/12*     (2006.01)
    *G06T 7/11*     (2017.01)
    *G06T 7/174*     (2017.01)
    *G06T 7/194*     (2017.01)
    *A61B 6/02*     (2006.01)

(52) U.S. Cl.
    CPC .......... *A61B 6/5235* (2013.01); *A61B 6/5252* (2013.01); *A61N 5/107* (2013.01); *A61N 5/1067* (2013.01); *G06T 7/11* (2017.01); *G06T 7/174* (2017.01); *G06T 7/194* (2017.01); *G06T 11/008* (2013.01); *A61B 6/022* (2013.01); *A61B 6/486* (2013.01); *A61N 2005/1061* (2013.01); *A61N 2005/1062* (2013.01); *G06T 2207/10016* (2013.01); *G06T 2207/10116* (2013.01); *G06T 2207/10124* (2013.01); *G06T 2207/30008* (2013.01)

(58) Field of Classification Search
    CPC .......... G06T 2207/20224; A61B 6/486; A61B 6/5217; A61B 6/5235; A61B 6/5252; A61N 5/1049; A61N 2005/1061; A61N 2005/1062
    See application file for complete search history.

(56) References Cited

U.S. PATENT DOCUMENTS

| | | | |
|---|---|---|---|
| 2009/0214099 A1* | 8/2009 | Merlet | 382/132 |
| 2014/0243579 A1* | 8/2014 | Roeske et al. | A61N 5/1039 600/1 |
| 2015/0018595 A1 | 1/2015 | Taguchi et al. | A61N 5/1067 |
| 2015/0025295 A1 | 1/2015 | Sugiura et al. | A61N 5/1049 |
| 2015/0045605 A1 | 2/2015 | Hirai et al. | A61N 5/103 |
| 2015/0094516 A1 | 4/2015 | Taguchi et al. | G06T 7/0044 |
| 2015/0117605 A1 | 4/2015 | Sugiura et al. | A61N 5/1049 |
| 2015/0154752 A1 | 6/2015 | Hirai et al. | G06T 7/0014 |
| 2015/0154757 A1 | 6/2015 | Sakata et al. | G06T 7/0026 |
| 2015/0164454 A1* | 6/2015 | Grant et al. | A61B 6/505 378/5 |
| 2015/0279111 A1 | 10/2015 | Sugiura et al. | G06T 19/006 |
| 2015/0287189 A1 | 10/2015 | Hirai et al. | G06T 7/0012 |

FOREIGN PATENT DOCUMENTS

| DE | 10 2013 214 479 A1 | 1/2015 | ............... G06T 7/00 |
|---|---|---|---|
| EP | 2 889 002 B1 | 7/2016 | ............... A61B 6/00 |

OTHER PUBLICATIONS

Shinichiro Mori et al. "Current Status and Future Prospects of Multi-Dimensional Image-Guided Particle Therapy", Radiol Phys Technol, vol. 6, 2013, 24 pages.

Shinichiro Mori et al. "Patient Handling System for Carbon Ion Beam Scanning Therapy", Journal of Applied Clinical Medical Physics, vol. 13, No. 6, 2012, 12 pages.

* cited by examiner

APPARATUS, METHOD, AND PROGRAM FOR PROCESSING MEDICAL IMAGE, AND RADIOTHERAPY APPARATUS

CROSS-REFERENCE TO RELATED APPLICATIONS

This application is based upon and claims the benefit of priority from Japanese Patient application No. 2014-234672, filed on Nov. 19, 2014, the entire contents of each of which are incorporated herein by reference.

BACKGROUND OF THE INVENTION

Field of the Invention

The present invention relates to a medical image processing technique for processing a radiograph of an inside of a body of a patient and a radiotherapy apparatus using the same.

Description of the Related Art

In radiotherapy performed as a treatment by emitting radiation to an affected part of the patient, the affected part may change over time with respiration, heart beats, motions of intestines and internal gas, and the like in some cases. In such a case, the motion of the affected part is tracked to determine proper timing of emission of radiation, or radiation is emitted while the affected part is traced.

To track such a changeable affected part, a tracking scheme is known in which the affected part is tracked based on an X-ray radiograph showing the periphery of the affected part.

This scheme has a problem that a bone reflected in the radiograph lowers detection accuracy of a tracking target. To cope with this problem, a medical image processing technique is considered to be useful. The medical image processing technique generates, from an X-ray radiograph, a radiograph showing only bone and/or a radiograph with the bone removed. For example, in Patent Document 1 (U.S. Pat. No. 7,545,965), a radiograph is used to generate a radiograph showing only the bone. The radiograph showing only the bone is subtracted from the original radiograph to generate a radiograph without the bone.

However, the scheme of Patent Document 1 needs prior learning using a pair of radiographs as teacher images, the pair of radiographs being a radiograph and a radiograph showing only the bone, which are acquired in advance with a dual-energy X-ray imaging apparatus.

It is concerned that the scheme using the teacher images may cause deterioration in performance of medical image processing in the case where radiography conditions are different between the teacher images and a processing target image. Furthermore, there is a problem that a person who is an object of the teacher images is contaminated by radioactivity.

Note that the radiograph includes the meaning of radiographic image, fluoroscopic image and digitally reconstructed radiograph (DRR).

SUMMARY OF THE INVENTION

In consideration of such circumstances, an object of embodiments of the present invention is to provide a medical image processing technique that can provide a radiograph with a part such as bone being removed at high accuracy or a radiograph with parts other than the part such as bone being removed at high accuracy, regardless of radiography conditions and without teacher images.

Another object of the embodiments is to provide a radiotherapy apparatus using the medical image processing technique, the apparatus being capable of precisely recognizing a position of an affected part movable by respiration and other factors and emitting medical radiation only to the affected part so as to minimize an influence on healthy cells. Here, the medical radiation includes X-rays, γ rays, electron beams, proton beams, neutron beams, and heavy particle beams. Hereinafter, the medical radiation may also be referred to as a beam.

A medical image processing apparatus according to the embodiments of the present invention includes: a first acquisition unit; a second acquisition unit; and a part-removed image generation unit, wherein the first acquisition unit is adapted to acquire a first radiograph that is a virtual radiograph generated to have a specified part or a predetermined part, among parts included in volume data indicative of a three-dimensional structure of an inside of a body of a patient, being emphasized, the second acquisition unit is adapted to acquire a second radiograph of the inside of the body of the patient, and the part-removed image generation unit is adapted to generate a part-removed image by removing the specified or predetermined part or parts other than the specified or predetermined part from the second radiograph with reference to the first radiograph.

The radiotherapy apparatus according to the embodiments of the present invention includes: a radiograph imaging unit; a movement amount calculation unit; a treatment table moving unit; an identification unit; and a beam emission unit, wherein the radiograph imaging unit is adapted to image the second radiograph acquired by the second acquisition unit, the movement amount calculation unit is adapted to calculate a movement amount of a treatment table with the patient mounted thereon, based on the imaged second radiograph, the treatment table moving unit is adapted to move the treatment table in accordance with the movement amount, the identification unit is adapted to identify a tracking target based on the part-removed image consecutively output from an external output unit of the medical image processing apparatus, and the beam emission unit is adapted to emit a beam that is medical radiation such as an X-ray and a heavy particle beam to an affected part of the patient at timing when the tracking target changing in the consecutive part-removed images in plural matches with an irradiation point of the beam, or the beam emission unit is adapted to emit the beam to the tracking target while tracking the tracking target.

The embodiments of the present invention provide a medical image processing technique that can provide a radiograph with a part such as bone being removed at high accuracy or a radiograph with parts other than the part such as bone being removed at high accuracy, regardless of radiography conditions and without teacher images.

Furthermore, the embodiments of the present invention provide a radiotherapy apparatus using the medical image processing technique, the apparatus being capable of precisely recognizing a position of an affected part movable by respiration and other factors and emitting a beam only to the affected part so as to minimize an influence on healthy cells.

DETAILED DESCRIPTION OF THE PREFERRED EMBODIMENTS

Embodiments of the present invention will be described hereinbelow with reference to the accompanying drawings.

Figure 1:
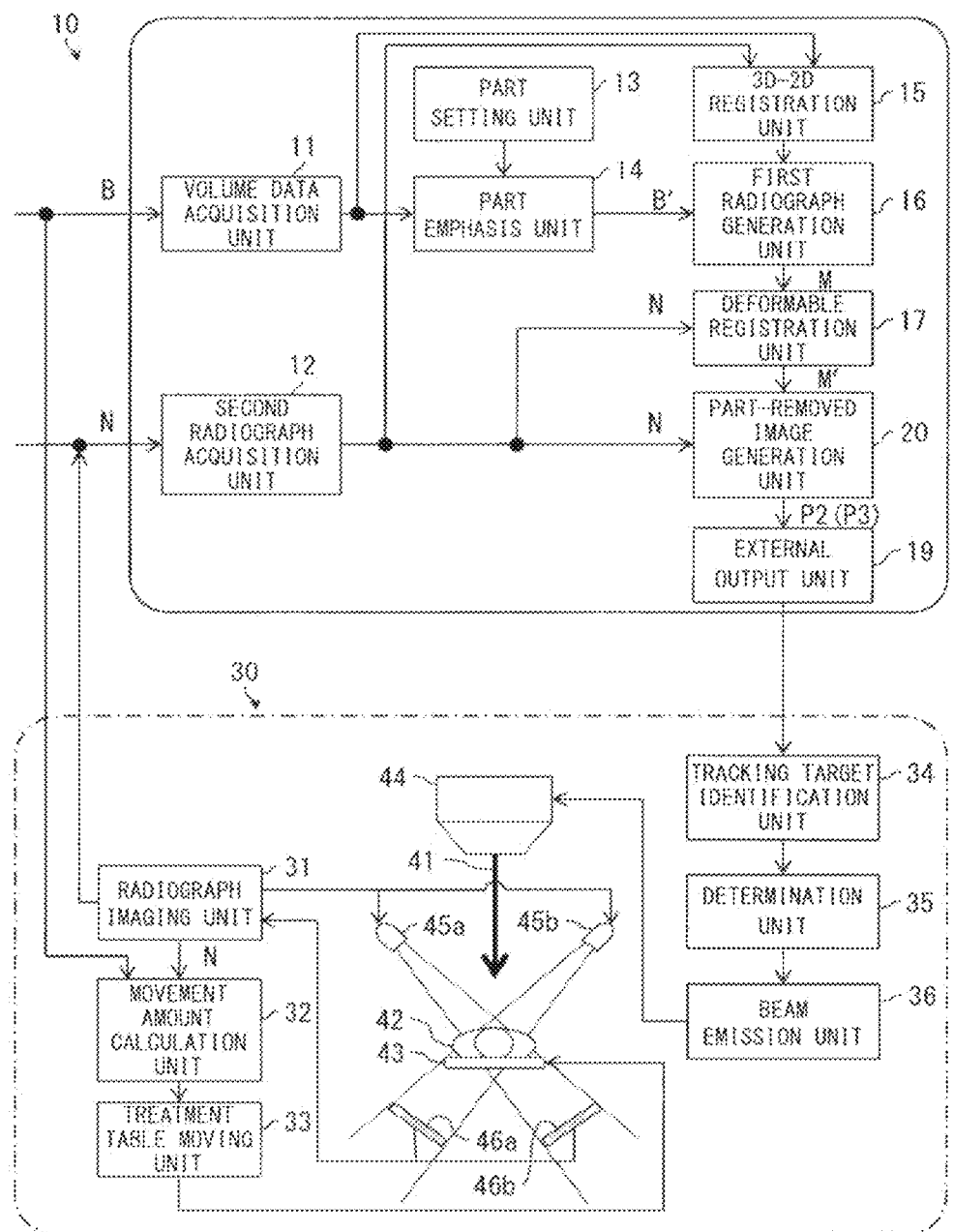
FIG. 1 is a block diagram illustrating a medical image processing apparatus and a radiotherapy apparatus using the same according to an embodiment of the present invention.

As illustrated in FIG. 1, a medical image processing apparatus 10 includes: a volume data acquisition unit 11 adapted to acquire volume data B indicative of a three-dimensional structure of an inside of a body of a patient; a part emphasis unit 14 adapted to generate volume data B' having an area of a specified part (for example, bone) being emphasized; a first radiograph generation unit 16 adapted to generate a first radiograph M as a virtual radiograph which is digitally reconstructed radiograph (DRR) based on the volume data B'; a second radiograph acquisition unit 12 adapted to acquire a second radiograph N showing the inside of the body of a patient 42 from a prescribed direction; and a part-removed image generation unit 20 adapted to remove a specified part (for example, bone) from the second radiograph N to generate a part-removed image P2, or to remove parts other than the specified part from the second radiograph N to generate a part-removed image P3.

In the medical image processing apparatus 10 of FIG. 1, a first acquisition unit 51 (see FIG. 12) positioned on an upstream side of the part-removed image generation unit 20 and adapted to acquire the first radiograph M (M') is omitted.

In the medical image processing apparatus 10, the second radiograph acquisition unit 12 consecutively acquires the second radiograph N. The medical image processing apparatus 10 further includes: a deformable registration unit 17 adapted to execute deformable registration for deforming the first radiograph M into a first radiograph M' on the basis of the acquired second radiograph N; and an external output unit 19 adapted to consecutively output a part-removed image P2 corresponding to the acquired second radiograph N to the outside.

A radiotherapy apparatus 30 includes: a radiograph imaging unit 31 adapted to image a second radiograph N acquired by the second radiograph acquisition unit 12 of the medical image processing apparatus 10; a treatment table moving unit 33 adapted to move a treatment table 43 with the patient 42 mounted thereon so that a set target is aimed; a tracking target identification unit 34 adapted to identify a tracking target based on the part-removed image P2 consecutively output from the external output unit 19 of the medical image processing apparatus 10; a determination unit 35 adapted to determine whether or not the tracking target changeable in the consecutive part-removed images in plural P2 matches with an irradiation point of a beam 41; and a beam emission unit 36 adapted to emit the beam at timing when the tracking target is determined to match with the irradiation point.

The volume data B acquired by the volume data acquisition unit 11 is a three-dimensional image of the inside of the body of the patient imaged with, for example, an X-ray CT scanner. In addition, the volume data B may also be an image imaged with an MRI apparatus. The volume data B may be any image indicative of the three-dimensional structure of the inside of the body of the patient.

If this volume data B is used, parts inside the body such as bone and various organs can be analyzable based on values of respective voxels.

In a part setting unit 13, names of various parts are listed in an information table. When a user hopes to remove or leave a certain part, the user can specify the name of the part, so that the part can be removed or left unremoved.

More specifically, in the part setting unit 13, the user specifies a part to be removed from or left in the second radiograph N (FIG. 3) in the end. Although the bone is specified in the embodiment, the part to be specified is not particular limited. When a part to be removed is predetermined, not the part specified by the user but the predetermined part may be set. In that case, the part setting unit 13 may be omitted. Hereinafter, the part set in the part setting unit 13 is stated as a set part.

The part emphasis unit 14 automatically determines, based on the values of the voxels, an area corresponding to the set part in the volume data B. The part emphasis unit 14 generates volume data B' by rewriting voxel values of the area corresponding to the set part in the first radiograph M generated in the first radiograph generation unit 16 so that the set part is emphasized.

For example, when the volume data B is CT data, the volume data B' is generated by setting the values of the voxels of the area corresponding to the set part to 1 and setting the values of the other voxels to 0. Or the volume data B' is generated by keeping the values of the voxels of the area corresponding to the set part unchanged while setting the values of the other voxels to 0.

The first radiograph generation unit 16 sets a virtual viewpoint and an image plane around the volume data B', and generates a first radiograph M that is a DRR of the volume data B' obtained by perspective projection.

The virtual viewpoint and the image plane of the first radiograph M are set by a 3D-2D registration unit 15. The 3D-2D registration unit 15 receives input of the volume data B and the second radiograph N. In the 3D-2D registration unit 15, the virtual viewpoint and the image plane similar in geometry to those used in photographing the second radiograph N (FIG. 3) are calculated by 3D-2D registration. By conducting the 3D-2D registration, positions of an object in the second radiograph N and the first radiograph M are aligned.

Figure 2:
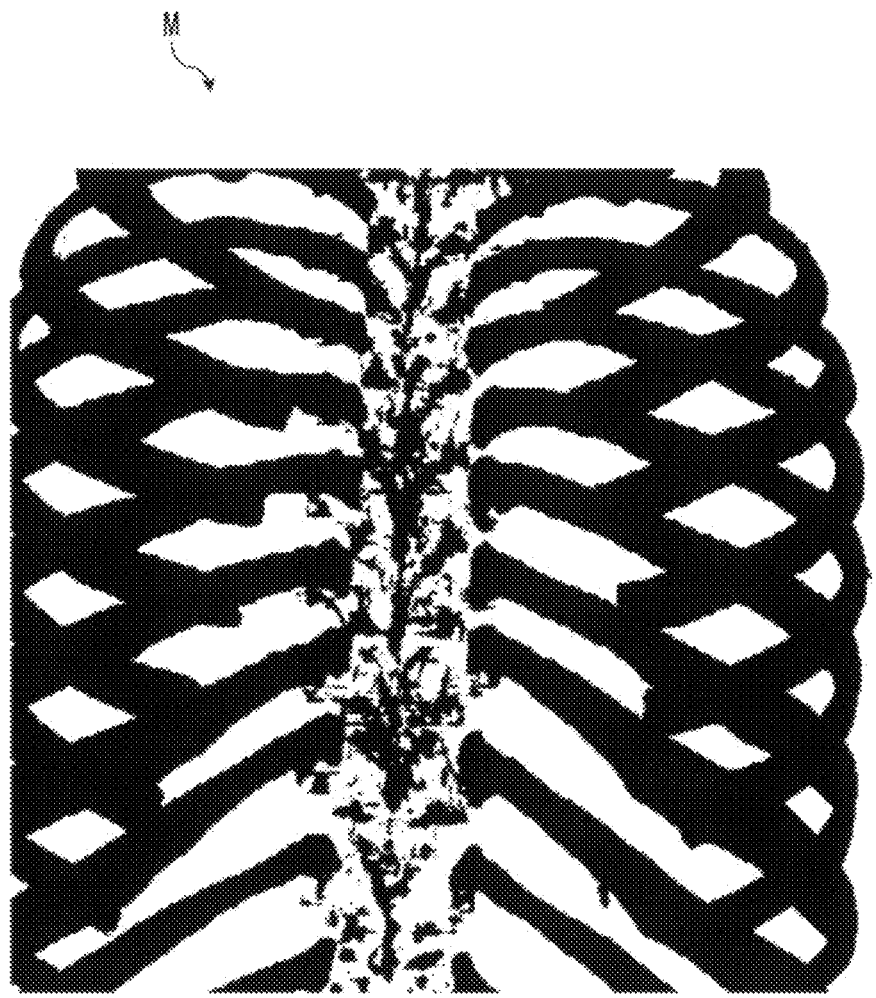
FIG. 2 illustrates a first radiograph that is a DRR with an area of bone included in volume data of a patient's chest being emphasized.

FIG. 2 illustrates an example of a first radiograph M of the volume data B' with bone as the set part being emphasized. FIG. 2 is a binary image expressing the bone in black and parts other than the bone in white. How the part area in the first radiograph M is emphasized is different depending on how the volume data B' in the part emphasis unit 14 is generated. For example, the first radiograph M may be a multi-valued image in which the area corresponding to the set part is shaded but other areas are not shaded and have only one value.

Since the first radiograph M that is a two-dimensional image is a perspective projection of the three-dimensional volume data B' onto an image plane, the emphasized area is an area of the set part (bone).

The first radiograph M generated in this way includes information indicating positions of the parts, which are to be removed from the second radiograph N, reflected on the second radiograph N.

Figure 3:
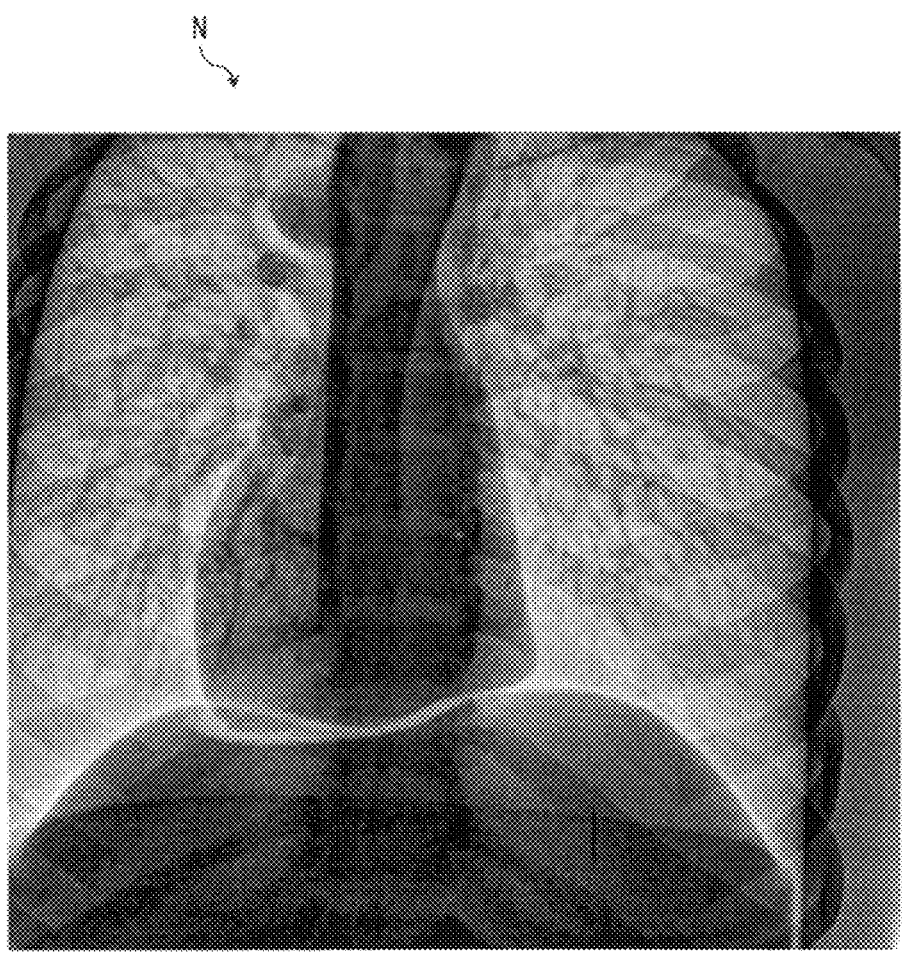
FIG. 3 illustrates a second radiograph of the patient's chest.

A second radiograph N illustrated in FIG. 3 is, for example, an X-ray radioscopic image, which is imaged with an apparatus configured to radiograph the inside of the body of the patient by emitting an X-ray from a predetermined position. Radiation other than the X-ray may be used for radiographing.

The thus-imaged second radiograph N is electronically transmitted and is acquired by the second radiograph acquisition unit 12.

The illustrated second radiograph N is an image of the patient 42 imaged in real time by an X-ray emission unit 45 and an X-ray detection unit 46 of the radiotherapy apparatus 30.

In this case, in a plurality of second radiographs N acquired over time by the second radiograph acquisition unit 12, a shape or a position of the set part (bone) sequentially change with respiration.

The first radiograph M and the second radiograph N do not necessarily coincide with each other in all the areas due to such factors as deviated photographing time, minor difference in posture on the bed, and deviation in phase of respiration, even though an identical patient is photographed.

Accordingly, the deformable registration unit 17 executes deformable registration that deforms the first radiograph M into a first radiograph M' on the basis of the acquired second radiograph N.

As a consequence, the position of the object in the first radiograph M' coincides with the position in the second radiograph N.

When the positions of the object in the first radiograph M and the second radiograph N coincide, it is not necessary to execute the deformable registration.

Even when the positions do not perfectly coincide, the deformable registration unit 17 is still omissible. To omit the unit 17, the first radiograph M is adopted instead of the first radiograph M'. Omitting the deformable registration unit 17 when the positions do not perfectly coincide may cause deteriorated display quality of the part-removed image.

Here, tissue information about a plurality of parts inside the body (skin, bone, internal organs, blood vessels, bronchial tubes, and the like), which are penetrated by radiation that reaches each pixel of the X-ray detection unit 46, is superimposed on pixels constituting the second radiograph N.

Accordingly, if some of the tissue information (bone information) included in the values of the respective pixels of the second radiograph N are removed, it becomes possible to obtain a radiograph with the corresponding part inside the body (bone) being removed.

The part-removed image generation unit 20 generates a part-removed image P2 by removing the set part (bone) from the second radiograph N.

According to this part-removed image P2, it becomes possible to enhance visibility of other body tissues (an affected part) which are difficult to visually recognize due to the existence of some parts (bone) in the second radiograph N.

Figure 4:
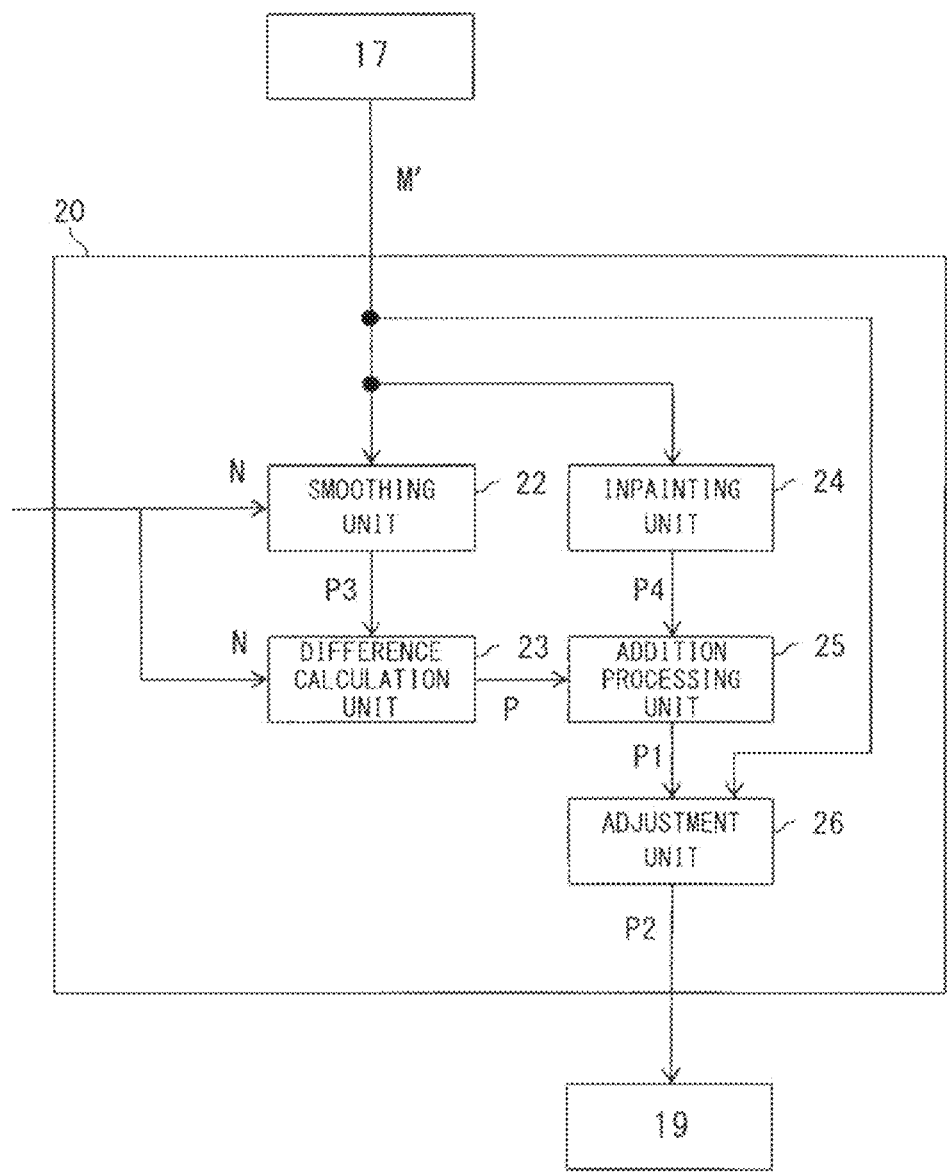
FIG. 4 is a block diagram illustrating an internal configuration of a part-removed image generation unit in the medical image processing apparatus according to the embodiment.

As illustrated in FIG. 4, the part-removed image generation unit 20 has a smoothing unit 22 adapted to generate a part-removed image P3 with parts other than the set part (bone) being removed, and a difference calculation unit 23 adapted to execute difference calculation of the second radiograph N and the part-removed image P3 to generate a part-removed image P.

The part-removed image generation unit 20 further has: an inpainting unit 24 adapted to generate a part-removed image P4 excluding both the set part (bone) and minute image patterns; an addition processing unit 25 adapted to add the part-removed image P to the part-removed image P4 to generate a part-removed image P1; and an adjustment unit 26 adapted to remove artifact noise from the part-removed image P1 or to perform image adjustment of the part-removed image P1 to generate a part-removed image P2.

Figure 5A:
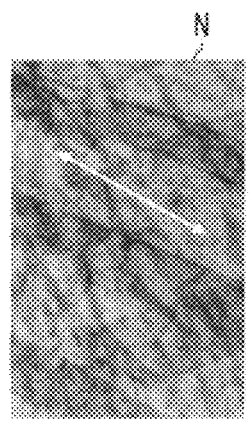
FIGS. 5A, 5B and 5C are explanatory views illustrating processes of image processing in the part-removed image generation unit.
Figure 5A:
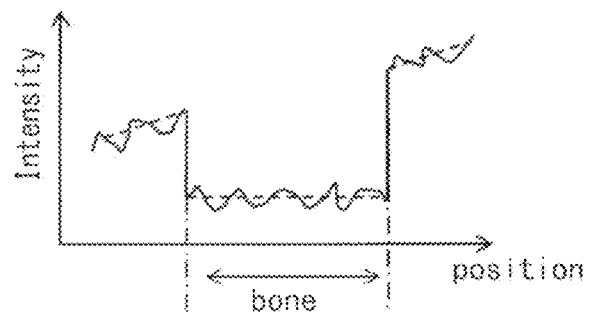

A left-side image of FIG. 5A illustrates a partial cutaway view of the second radiograph N (FIG. 3). A right-side graph view of FIG. 5A is a schematic view illustrating intensity of the pixels on a line segment extending on the left-side image. A horizontal axis of the graph view represents a position on the line segment, and a vertical axis represents intensity.

As illustrated in the graph view, a portion in the vicinity of the center of the line segment where bone is plotted has an intensity relatively smaller than portions (lung field) on both sides of the line segment where bone is not plotted. Furthermore, according to the graph, the presence of image patterns originating from other body tissues (bronchial tubes and the like) is recognized irrespective of the presence of the bone.

Figure 5B:
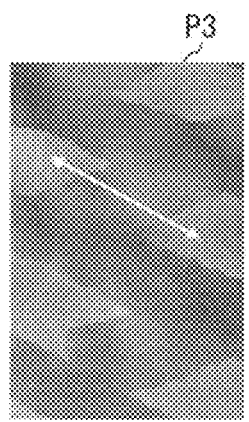
Figure 5B:
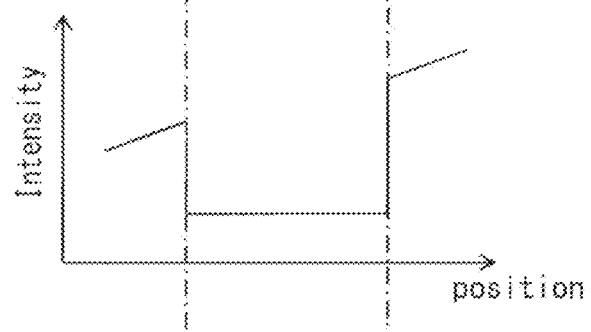

A left-side image of FIG. 5B illustrates partial region of a part-removed image P3. An example of the smoothing unit 22 will be described with reference to a flowchart of FIG. 7.

Figure 7:
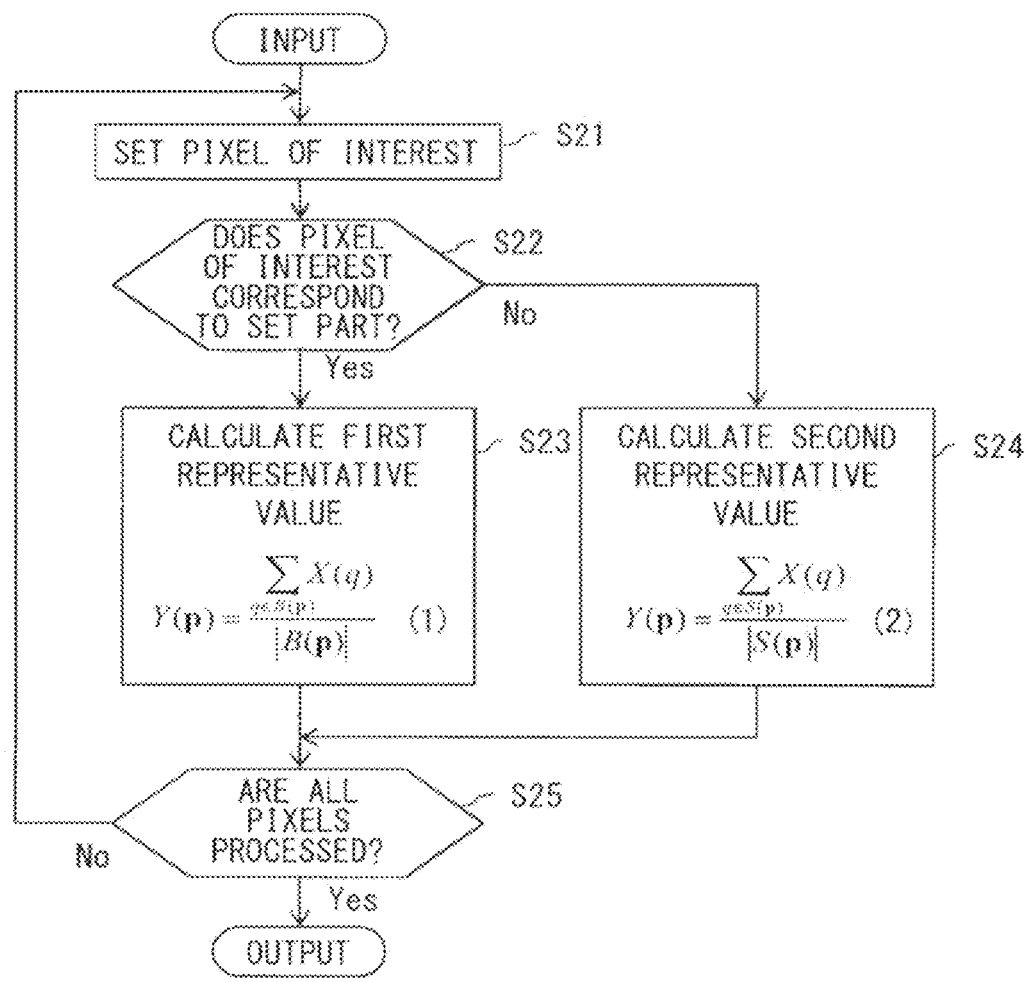
FIG. 7 is an explanatory view illustrating an example of a smoothing unit constituting the part-removed image generation unit.

Any one of the plurality of pixels constituting the second radiograph N (FIG. 5B) is set as a pixel of interest (S21). Whenever the flow in FIG. 7 is repeated, the pixel of interest shifts to another adjacent pixel on the second radiograph N.

When the pixel of interest corresponds the set part (bone) (Yes in S22), a first representative value Y(p) is calculated in accordance with a calculation formula (1) that calculates an average of the values of the pixels representing the set part (bone), and the calculated first representative value Y(p) is set as a value of the pixel of interest of the part-removed image P3 (S23). When the pixel of interest does not represent the set part (bone) (No in S22), a second representative value Y(p) is calculated in accordance with a calculation formula (2) that calculates an average of the values of the pixels not representing the set part (bone), and the calculated second representative value Y(p) is set as a value of the pixel of interest of the part-removed image P3 (S24).

Here, whether or not the pixel of interest represents the set part (bone) is determined with reference to the first radiograph M'. In the formulas, p represents a position vector of the pixel of interest, X(q) represents a value of a pixel of interest q that is defined as a pixel in the periphery of p, Ω(p) (see FIG. 8) represents a set of pixels in the periphery of the pixel of interest, B(p) represents a set of pixels representing the set part (bone) among the pixels included in Ω(p), and S(p) represents a set of pixels not representing the set part (bone) among the pixels included in Ω(p). Terms |B(p)| and |S(p)| represent the number of elements of the set B(p) and the set S(p), respectively.

Furthermore, Ω(p) represents a union of the sets B(p) and S(p).

After the representative value Y(p) is calculated for all the pixels included in the second radiograph N (Yes in S25), a part-removed image P3 is output. The part-removed image P3 is a part-removed image formed by removing parts other than the set part (bone) from the second radiograph N.

A right-side graph view of FIG. 5B is a schematic view illustrating intensity of the pixels on a line segment extending on a part-removed image P3 on the left-side of FIG. 5B. A horizontal axis of the graph view represents a position on the line segment, and a vertical axis represents intensity.

As indicated in the graph view, the part-removed image P3 is free from minute image patterns originating from body tissues (bronchial tubes and the like) other than the set part (bone).

Another example of the smoothing unit 22 will be described with reference to a flowchart of FIG. 8.

Any one of the plurality of pixels constituting the part-removed image P3 (FIG. 5B) is set as a pixel of interest (S31). Whenever the flow of FIG. 8 is repeated, the pixel of interest shifts to another adjacent pixel on the part-removed image P3.

Or any one of the plurality of pixels constituting the second radiograph N (FIG. 5A) is set as a pixel of interest (S31). Whenever the flow of FIG. 8 is repeated, the pixel of interest shifts to another adjacent pixel on the second radiograph N.

A third representative value Y(p) is calculated in accordance with a calculation formula (3), irrespective of whether or not the pixel of interest represents the set part (bone) (S32).

In the formula, q represents a pixel in Ω(p), and w(q) represents a weight applied to each of the pixels q in Ω(p). The weight coefficient w(q) is set to be larger as the value of the pixel of interest p in the first radiograph M' is closer to the value of the pixel q in the first radiograph M'.

For example, when the pixel of interest p represents the set part (bone), and the pixel q does not represent the set part (bone), the values of the pixel of interest p and the pixel q are different from each other, so that the weight coefficient w(q) takes a small value.

On the contrary, when both the pixel of interest p and the pixel q represent the set part (bone), or when neither the pixel of interest p nor the pixel q represent the set part (bone), the values of the pixel of interest p and the pixel q are close to each other, so that the weight coefficient w(q) takes a large value.

After the third representative value Y(p) is calculated for all the pixels included in the second radiograph N (Yes in S33), a part-removed image P3 is output. The part-removed image P3 is a part-removed image formed by removing parts other than the set part (bone) from the second radiograph N.

Figure 5C:
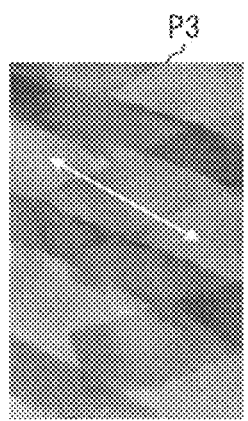
Figure 5C:
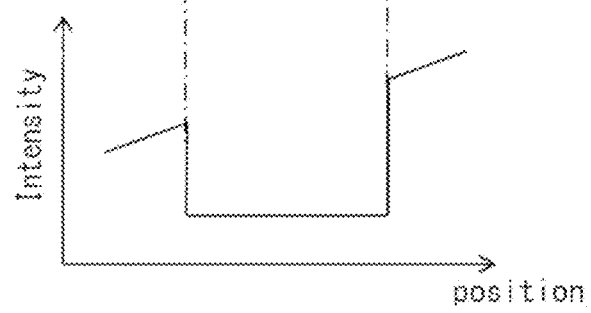

A left-side image of FIG. 5C illustrates part of a part-removed image P3 smoothed by another example of the smoothing unit 22 (FIG. 4) described before.

A right-side graph view of FIG. 5C is a schematic view illustrating intensity of a pixel Y(p) on a line segment extending on the part-removed image P3. A horizontal axis of the graph view represents a position on the line segment, and a vertical axis represents intensity.

It is confirmed that the case of FIG. 5C can also provide the result similar to FIG. 5B.

The calculation formulas (1) and (2) for calculating an average value of each region and the calculation formula (3) for calculating a weighted average efficiency have been illustrated as a method for calculating the representative value Y(p) in the smoothing unit 22. However, the method is not limited to the methods disclosed. The average value in each region calculated in the formulas (1) and (2) may be replaced with a median value in each region or a mode value in each region. A weighted median value may be adopted instead of the weighted average efficiency calculated in the calculation formula (3). Since the first radiograph M' is referred in either case, an edge preserving smoothing filter is provided. To calculate the representative value Y(p), other smoothing filters which refer to the first radiograph M' may be used. Examples of the smoothing filters include a bilateral filter, an epsilon filter, and a guided image filter. By performing smoothing with reference to the first radiograph M', the edge preserving smoothing filter is provided.

Figure 9:
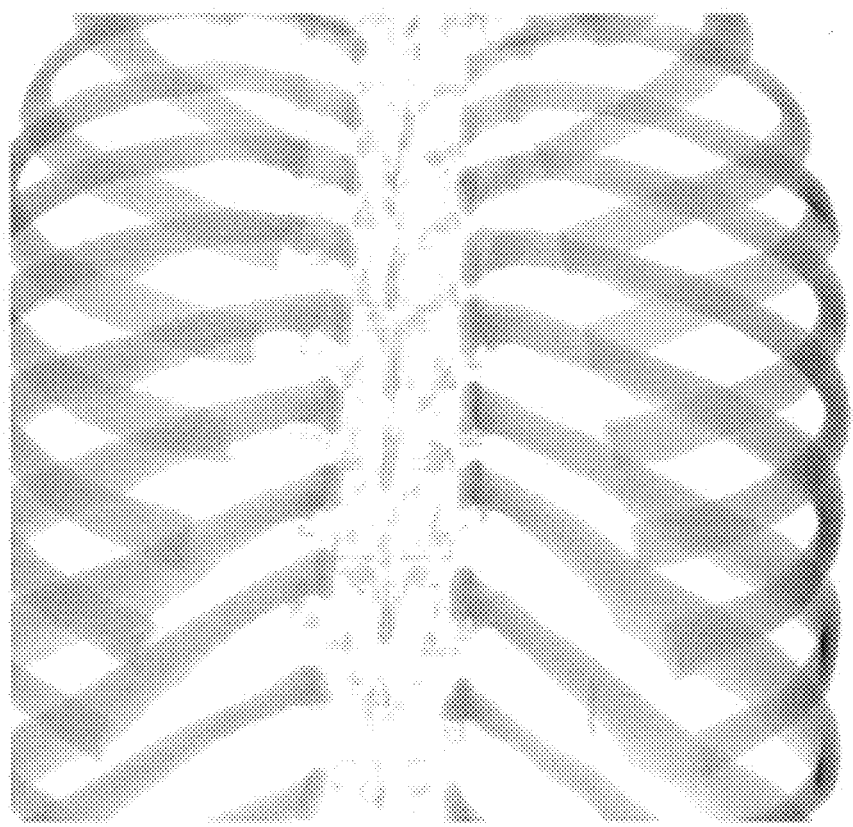
FIG. 9 is a schematic view illustrating one example of a part-removed image P3.

Thus, the part-removed image P3 smoothed in the smoothing unit 22 (FIG. 4) is a part-removed image formed by removing the parts other than the set part (bone) from the second radiograph N as illustrated in FIG. 9.

The difference calculation unit 23 (FIG. 4) executes difference calculation of the pixels constituting the part-removed image P3 and the pixels constituting the second radiograph N. An image output as a result of executing the difference calculation is a part-removed image P that is the second radiograph N with the set part (bone) being removed.

Figure 6A:
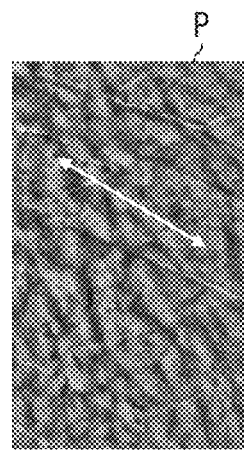
FIGS. 6A, 6B and 6C are explanatory views illustrating processes of image processing in the part-removed image generation unit.
Figure 6A:
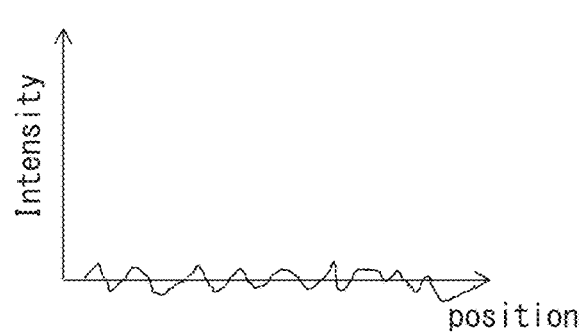

A left-side image of FIG. 6A illustrates part of a part-removed image P. A right-side graph view of FIG. 6A is a schematic view illustrating intensity of the pixels on a line segment extending on the left-hand side image. A horizontal axis of the graph view represents a position on the line segment, and a vertical axis represents intensity.

As indicated in the graph view, the part-removed image P with the bone being removed clearly shows image patterns originating from other body tissues (bronchial tubes and the like), the presence of which is difficult to sense while the bone is depicted. In other words, it becomes possible to enhance the visibility of other tissues which are difficult to recognize in the state of overlapping with another body tissue. The part-removed image P may have negative values.

The inpainting unit 24 (FIG. 4) generates a part-removed image P4 by removing the set part (bone) and other minute image patterns from the second radiograph N with reference to the first radiograph M'.

Figure 10:
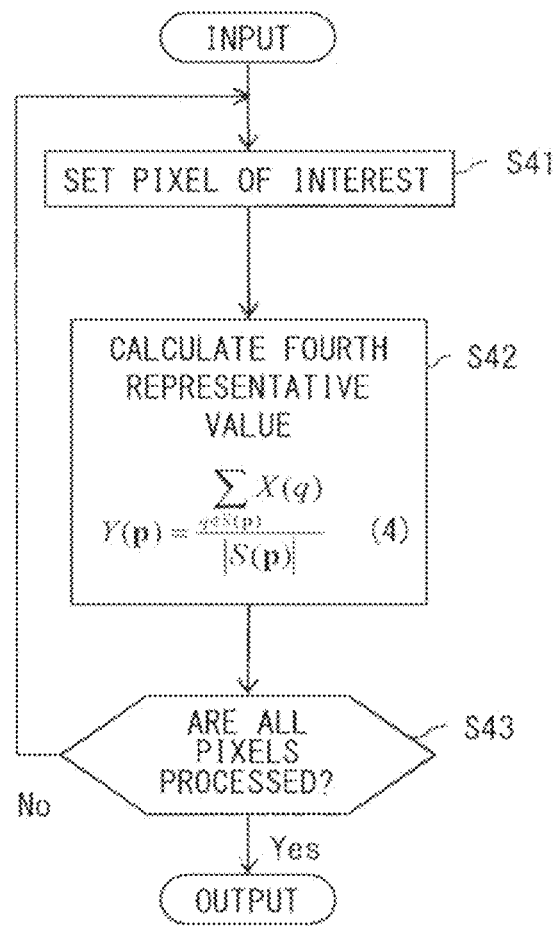
FIG. 10 is an explanatory view illustrating an example of an inpainting unit constituting the part-removed image generation unit.

Operation of the inpainting unit 24 will be described with reference to a flowchart of FIG. 10.

Any one of the plurality of pixels constituting the second radiograph N (FIG. 5B) is set as a pixel of interest (S41). Whenever the flow of FIG. 10 is repeated, the pixel of interest shifts to another adjacent pixel on the second radiograph N.

A fourth representative value Y(p) is calculated in accordance with a calculation formula (4), irrespective of whether or not the pixel of interest represents the set part (bone) (S42).

Figure 8:
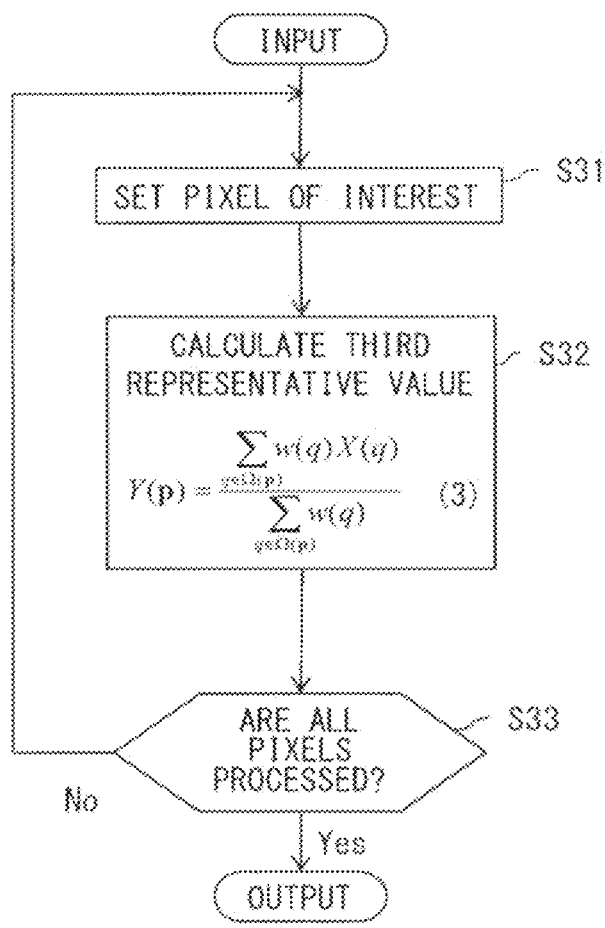
FIG. 8 is an explanatory view illustrating another example of the smoothing unit constituting the part-removed image generation unit.

More specifically, the fourth representative value Y(p) is generated based on a set of pixels S(p) not representing the set part (bone) in the set of pixels Ω(p) in the periphery of the pixel of interest p (see the FIG. 8). According to the calculation formula (4) of the fourth representative value Y(p), an average value of one or more pixels included in the set of pixels S(p) is calculated. Instead of the average value used in the calculation formula (4), values such as a weighted average efficiency, a median value, a weight median value, and a mode value may be used.

Accordingly, when the pixel of interest p represents the set part (bone), the fourth representative value Y(p) is a value inpainted from surrounding pixels not representing the set part (bone).

When the pixel of interest p does not represent the set part (bone), the fourth representative value Y(p) takes a value obtained by smoothing the values of surrounding pixels not representing the set part (bone).

After the fourth representative value Y(p) is calculated for all the pixels included in the second radiograph N (Yes in S43), a part-removed image P3 is output.

Figure 6B:
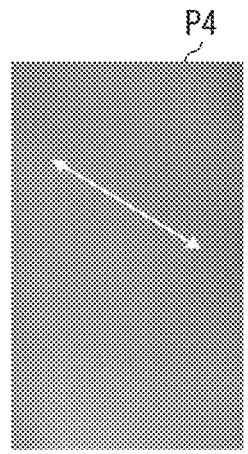
Figure 6B:
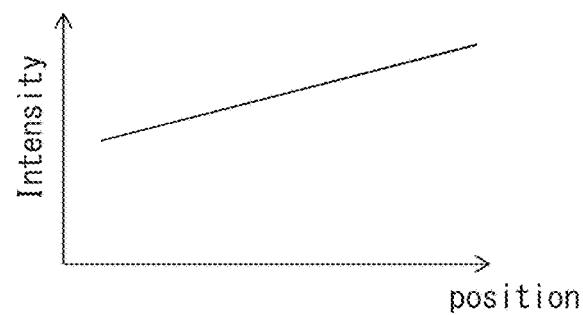

A left-side image of FIG. 6B illustrates part of a part-removed image P4 conversion-processed by the aforementioned inpainting unit 24 (FIG. 4).

A right-side graph view of FIG. 6B is a schematic view illustrating intensity of a pixel Y(p) on a line segment extending on the part-removed image P4. A horizontal axis of the graph view represents a position on the line segment, and a vertical axis represents intensity.

Thus, the inpainted part-removed image P4 is a part-removed image with the bone and other tissues (bronchial tubes and the like) being removed.

The addition processing unit 25 (FIG. 4) adds the pixels constituting the part-removed image P, and the pixels constituting the part-removed image P4.

Figure 6C:
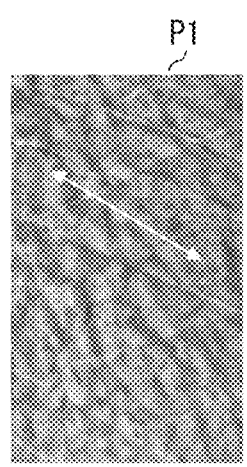
Figure 6C:
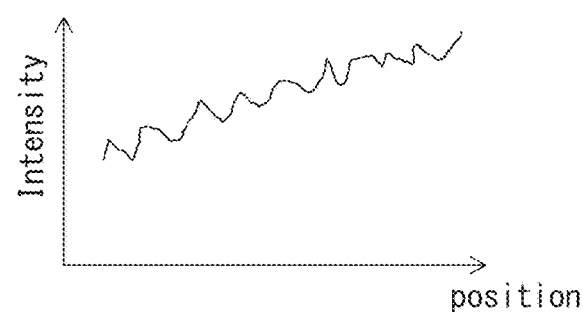

A left-side image of FIG. 6C illustrates part of a part-removed image P1 addition-processed by the aforementioned addition processing unit 25 (FIG. 4).

A right-side graph view of FIG. 6C is a schematic view illustrating intensity of a pixel Y(p) on a line segment extending on the part-removed image P1. A horizontal axis of the graph view represents a position on the line segment, and a vertical axis represents intensity.

The part-removed image P1 addition-processed in this way is an image without any negative value since the bone is removed so that the body tissues (bronchial tubes and the like) other than the bone are clear.

The adjustment unit 26 removes artifact noise from the part-removed image P1 or performs image adjustment of the part-removed image P1 to generate and output a part-removed image P2.

The artifact noise herein refers to unevenness in intensity generated in the vicinity of boundaries between the set part (bone) and other parts when the 3D-2D registration unit 15 or the deformable registration unit 17 has insufficient accuracy.

In this case, the artifact noise can be reduced by smoothing the intensity in the vicinity of the boundaries. Since the information on the boundaries is included in the first radiograph M', the artifact noise is reduced by smoothing the intensity with reference to the first radiograph M'.

Examples of the image adjustment include emphasizing and attenuating mage patterns by using an unsharp mask filter or a Gaussian filter, which can enhance the visibility of body tissues.

Although the adjustment unit 26 is placed subsequent to the addition processing unit 25 in FIG. 4, the adjustment unit 26 may be placed in other positions or the plurality of adjustment units 26 may be placed. For example, the adjustment unit 26 may be placed subsequent to the difference calculation unit 23 to process the part-removed image P.

In the aforementioned processing for removing the set part (bone) in the part-removed image generation unit 20, the values of the pixels not representing the set part (bone) may be changed from the values of the second radiograph N. The processing may be modified so that the pixels not representing the set part (bone) take original values of the second radiograph N with reference to the first radiograph M.

In the aforementioned processing for removing the parts other than the set part (bone) in the part-removed image generation unit 20, the values of the pixels representing the set part (bone) may be changed from the values of the second radiograph N. The processing may be changed so that the pixels representing the set part (bone) take original values of the second radiograph N with reference to the first radiograph M'.

The external output unit 19 (FIG. 1) outputs the part-removed image P2 output from the part-removed image generation unit 20 to the outside. When the plurality of second radiographs N are consecutively acquired in the second acquisition unit 12, the external output unit 19 consecutively outputs corresponding part-removed images P2 to the outside in synchronization with the acquisition.

The external output unit 19 may output not the part-removed image P2 but any one of the part-removed image P, P1, P3 and P4. When an output from the external output unit 19 is changed to other than the part-removed image P2, unnecessary components may be removed from the part-removed image generation unit 20. For example, when an output from the external output unit 19 is changed to the part-removed image P, the inpainting unit 24, the addition processing unit 25, and the adjustment unit 26 which are not useful in generating the part-removed image P are not necessary for the part-removed image generation unit 20.

The medical image processing apparatus 10 described in the foregoing includes a dedicated chip, a control device such as a field programmable gate array (FPGA), a graphics processing unit (GPU), or a central processing unit (CPU), a storage device such as a read only memory(ROM) and a random access memory (RAM), an external storage device such as a hard disk drive (HDD) and a solid state drive (SSD), a display device such as a display unit, an input device such as a mouse and a keyboard, and a communication I/F. The medical image processing apparatus 10 can be implemented by hardware configuration using a general computer.

A program executed in the medical image processing apparatus 10 is provided preinstalled in a ROM or other memory devices. Or the program may be stored in a computer readable storage medium such as a CD-ROM, a CD-R, a memory card, a DVD, and a flexible disk (FD) and be provided as a file in an installable or executable format.

The program executed in the medical image processing apparatus 10 according to the present embodiment may be stored on a computer connected to a network such as the Internet and be provided through downloading via the network.

The description will be continued with reference to FIG. 1 again.

The radiotherapy apparatus 30 takes a shot at an affected part inside the body of the patient 42 with the treatment beam 41 for treatment of the affected part.

When the beam 41, which is a heavy particle beam, enters the body, the beam 41 loses its kinetic energy in the process of passing the body. Once the beam 41 slows down to a certain prescribed rate, it suddenly stops and generates a large dose of radiation called a Bragg peak. With the large dose of radiation generated at a pinpoint in this way, only cancer cells can be shot and killed while influence on healthy cells can be minimized.

Accordingly, the treatment technique using the heavy particle beam 41 has excellent features of high therapeutic effects on malignant tumors such as cancer, low side effects, reduced load to the body, and the like.

Regardless of the types of the treatment beam 41, the radiotherapy apparatus 30 is required to accurately aim the beam 41 to be emitted to the affected part so as to prevent normal tissues from being damaged.

Accordingly, a position of the affected part is specified by X-ray observation and the like before emission of the beam, and a position and an angle of the movable treatment table 43 with the patient mounted thereon are appropriately adjusted by the moving unit 33, so that the affected part is accurately positioned within an emission range of the beam 41.

The radiograph imaging unit 31 controls the X-ray emission unit 45 (45a, 45b) and the X-ray detection unit 46 (46a, 46b) to image a second radiograph N of the patient 42.

The second imaged radiograph N is sent to the movement amount calculation unit 32 to be used for generating a movement amount of the treatment table moving unit 33 necessary for aiming the beam 41 at the affected part. The second imaged radiograph N is also acquired by the second acquisition unit 12.

When the beam 41 is emitted to an affected part which is present in an internal organ with motion (lung and the like), it is necessary to determine emission timing in consideration of periodic displacement caused by respiration, heart beats and the like to ensure the accuracy of beam emission.

In such a case, in addition to the method for directly aiming the beam 41 at the affected part, a method for embedding a gold marker or the like in the vicinity of the affected part, tracking movement of the marker with the aid of X-ray photography, and identifying the position of the affected part is adopted.

The identification unit 34 identifies the tracking target (affected part or marker) based on the part-removed image P2 consecutively output from the external output unit 19 of the medical image processing apparatus 10.

The determination unit 35 determines whether or not the tracking target changing in the consecutive part-removed images in plural P2 matches with the irradiation point of the beam 41.

The beam emission unit 36 emits the beam at timing when the tracking target is determined to match with the irradiation point. The beam 41 emitted to the patient 42 includes X-rays, γ rays, electron beams, proton beams, neutron beams, and heavy particle beams.

Figure 11:
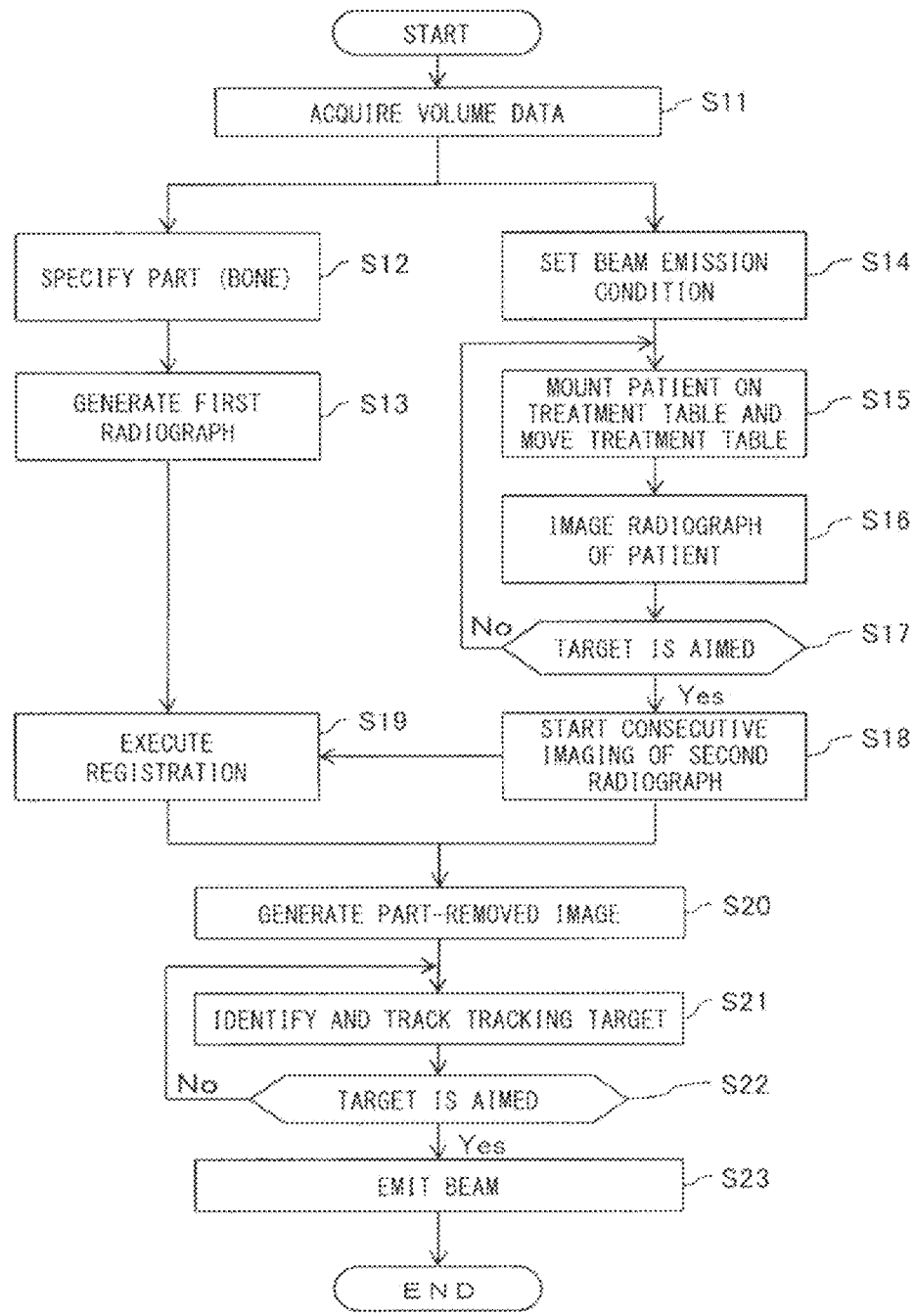
FIG. 11 is a flowchart illustrating operation in a method and a program for processing a medical image and a radiotherapy apparatus using the same according to the embodiment.

A description is given of operation in the method and program for processing a medical image according to the embodiment and the radiotherapy apparatus using the same with reference to the flowchart of FIG. 11 (see FIG. 1 as necessary).

The inside of the body of a patient is imaged with an X-ray CT scanner or the like to acquire volume data (S11). A part (bone) included in the volume data is set (S12), and a DRR with the set part being emphasized is generated from the volume data as a first radiograph M (S13).

In the meanwhile, the acquired volume data is used to recognize a position and a range of an affected part, and emission conditions for emitting the beam 41 to the affected part is set (S14).

The patient 42 is mounted on the treatment table 43 of the radiotherapy apparatus 30, and the treatment table 43 is moved directly below a muzzle 44 (S15).

In this state, the imaging unit 31 is operated to image a radiograph of the patient 42 (S16), so that the movement amount of the treatment table 43 necessary for aiming the beam 41 at the affected part is generated. Then, the treatment table 43 is moved until the affected part is aimed (No/Yes in S17).

The imaging unit 31 is operated again to start consecutive imaging of the second radiographs N of the patient 42 (S18).

The second radiograph N consecutively sent from the radiotherapy apparatus 30 is acquired in the medical image processing apparatus 10, and deformable registration is executed for the first radiograph M on the basis of each of the second radiographs N (S19).

A first radiograph M' generated by deformable registration is referred to generate a part-removed image P2 with bone being removed from the second radiograph N (S20), and the generated part-removed image P2 is transmitted to the radiotherapy apparatus 30.

The radiotherapy apparatus 30 identifies and tracks the tracking target (affected part or marker) out of the received part-removed images P2 (S21). At timing when the tracking target matches with an irradiation point (No/Yes in S22), the beam 41 is emitted (S23).

The emitted beam 41 generates a Bragg peak at the position of the affected part displaced to the irradiation point, and thereby treats cells of this affected part (END).

An output from the external output unit 19 may be changed from the part-removed image P2 to the part-removed image P or the part-removed image P1. Since the part-removed image P and the part-removed image P1 are free from the set part (bone), the tracking target (affected part or marker) is easily recognized. In the case where, for example, a diaphragm is set as a set part and a tracking target, an output from the external output unit 19 may be changed from the part-removed image P2 to the part-removed image P3 or the part-removed image P4. Since the parts other than the set part (diaphragm) are removed from the part-removed image P3 or the part-removed image P4, it is easy to track the diaphragm.

Although the radiotherapy apparatus 30 tracks the tracking target (affected part or marker) and emits the beam 41 at predetermined timing in the example disclosed, the radiotherapy apparatus 30 may track the affected part and emits the beam 41 while tracking the affected part.

Figure 12:
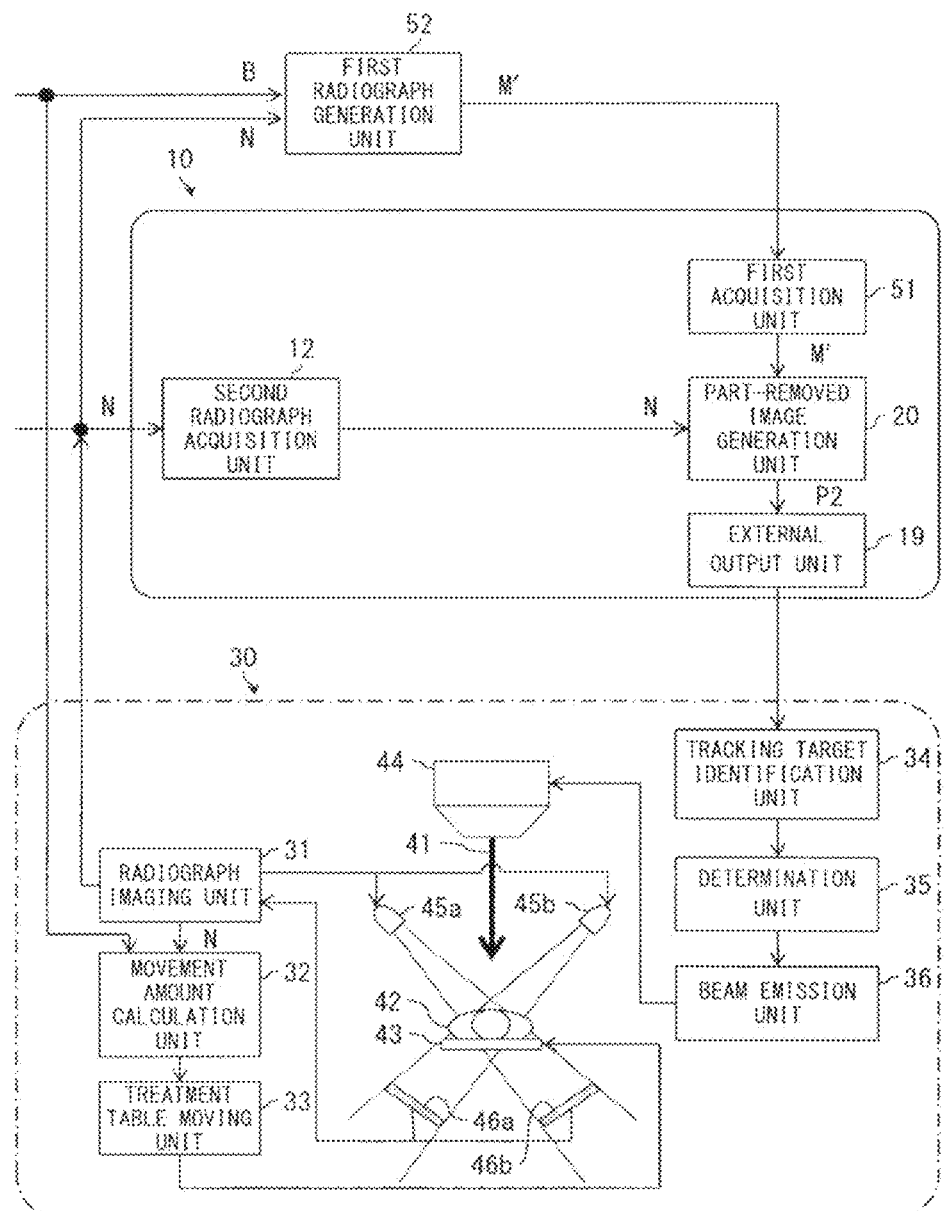
FIG. 12 is a block diagram illustrating a medical image processing apparatus and a radiotherapy apparatus using the same according to another embodiment of the present invention.

A description is now given of a medical imaging apparatus 10 according to another embodiment with reference to FIG. 12. In FIG. 12, component members common in configuration or function with those in FIG. 1 are designated by identical reference numerals to omit redundant description.

A first radiograph generation unit 52 includes, for example, a volume data acquisition unit 11, a part setting unit 13, a part emphasis unit 14, a 3D-2D registration unit 15, a first radiograph generation unit 16, and a deformable registration unit 17 of FIG. 1.

The medical imaging apparatus 10 includes a first acquisition unit 51, a second radiograph acquisition unit 12, a part-removed image generation unit 20, and an external output unit 19.

The first acquisition unit 51 acquires a first radiograph M', and sends it to the part-removed image generation unit 20. The first radiograph M' is generated outside of the medical imaging apparatus 10.

Although the first radiograph M' may be generated by units other than the first radiograph generation unit 52, the first radiograph M' is generated based on the volume data B and the second radiograph N.

Since what is input into the part-removed image generation unit 20 in both the medical image processing apparatus 10 of FIG. 1 and the medical imaging apparatus 10 of FIG. 12 is identical, what is output from the medical image processing apparatuses 10 is identical to what is output from the medical imaging apparatuses 10. Therefore, the medical imaging apparatus 10 of FIG. 12 also has effects similar to those of the medical image processing apparatus 10 of FIG. 1.

According to the medical image processing apparatus of the embodiments described in the foregoing, a part included in a second radiograph obtained by imaging a patient is specified by using a first radiograph generated based on volume data, so that a radiograph with the specified part such as bone being removed at high accuracy can be provided regardless of radiography conditions and without teacher images. Furthermore, the radiotherapy apparatus of the embodiments can precisely recognize a position of an affected part movable by respiration and other factors and emit a beam only to the affected part so as to minimize an influence on healthy cells.

Although some embodiments of the present invention have been described, these embodiments are in all respects illustrative and are not considered as the basis for restrictive interpretation. It should be understood that these embodiments can be performed in other various forms and that various removals, replacements, modifications, and combinations are possible without departing from the meaning of the present invention. These embodiments and their modifications are intended to be embraced in the range and meaning of the present invention, and are particularly intended to be embraced in the invention disclosed in the range of the claims and the equivalency thereof.

What is claimed is:

1. A medical image processing apparatus, comprising:
processing circuitry configured to
acquire a first radiograph that is a virtual radiograph representing a projection of volume data, the volume data representing a three-dimensional structure of an inside of a body of a patient, and the virtual radiograph being generated to emphasize a specified part or a predetermined part among parts indicative of the three-dimensional structure of the inside of body of the patient that are included in the volume data,
acquire a second radiograph of the inside of the body of the patient,
apply, to the second radiograph, a smoothing filter, the smoothing filter being based on the first radiograph, and
generate a part-removed image by removing one of the specified or predetermined part and other parts, which are parts other than the specified or predetermined part, wherein,
for a case in which the part-removed image is generated by removing the other parts, the part-removed image is generated from the second radiograph after the smoothing filter has been applied, and,
for a case in which the part-removed image is generated by removing the specified or predetermined part, the part-removed image is generated from a difference between the second radiograph before the smoothing filter has been applied and the second radiograph after the smoothing filter has been applied.

2. The medical image processing apparatus according to claim 1, wherein the processing circuitry is further configured to
acquire the second radiograph consecutively, and
consecutively output the part-removed image.

3. The medical image processing apparatus according to claim 1, wherein the processing circuitry is further configured to
acquire the volume data; and
generate the first radiograph, wherein
the acquiring of the volume data and the generating of the first radiograph are performed prior to the applying the smoothing filter and the generating of the part-removed image.

4. A radiotherapy apparatus, comprising:
the medical image processing apparatus according to claim 2; and
a radiograph imager including
a radiation source configured to emit radiation, and
detectors configured to detect the radiation from the radiation source; and
another processing circuitry configured to
generate, based on the detected radiation, the second radiograph, which is subsequently signaled to and acquired by the processing circuitry of the medical image processing apparatus,
calculate a movement amount of a treatment table with the patient being mounted thereon, based on the imaged second radiograph,
control the treatment table to move in accordance with the movement amount,
identify a tracking target based on the part-removed image consecutively output from the processing circuitry of the medical image processing apparatus, wherein
the radiation emitted by the radiation source is medical radiation, and the another processing circuitry is further configured to control the radiation source to either
emit the medical radiation to an affected part of the patient upon the tracking target identified in multiple of the consecutively output part-removed images matching a pointing-direction of the radiation emitted from the radiation source, or
emit the medical radiation to the tracking target while tracking the tracking target.

5. A method for processing a medical image, comprising:
acquiring a first radiograph that is a virtual radiograph representing a projection of volume data, the volume data representing a three-dimensional structure of an inside of a body of a patient, and the virtual radiograph being generated to ha emphasize a specified part or a predetermined part among parts indicative of the three-dimensional structure of the inside of the body of the patient that are included in the volume data,
acquiring a second radiograph of the inside of the body of the patient,
applying, to the second radiograph, a smoothing filter, the smoothing filter being based on the first radiograph, and
generating a part-removed image by removing one of the specified or predetermined part and other parts, which are parts other than the specified or predetermined part from the second radiograph with reference to the first radiograph, wherein,
for a case in which the part-removed image is generated by removing the other parts, the part-removed image is generated from the second radiograph after the smoothing filter has been applied, and, for a case in which the part-removed image is generated by removing the specified or predetermined part, the part-removed image is generated from a difference between the second radiograph before the smoothing filter has been applied and the second radiograph after the smoothing filter has been applied.

6. A non-transitory computer readable storage medium including executable instructions of a medical image processing program that, when executed by a computer, cause the computer to perform the method according to claim 5.

* * * * *